United States Patent
Nakamura et al.

(10) Patent No.: US 10,441,248 B2
(45) Date of Patent: Oct. 15, 2019

(54) ULTRASONIC DEVICE, PROBE, ELECTRONIC EQUIPMENT, AND ULTRASONIC IMAGE DEVICE

(71) Applicant: SEIKO EPSON CORPORATION, Tokyo (JP)

(72) Inventors: Tomoaki Nakamura, Nagano (JP); Yasunori Onishi, Nagano (JP); Tomohide Onogi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 644 days.

(21) Appl. No.: 14/525,623

(22) Filed: Oct. 28, 2014

(65) Prior Publication Data

US 2015/0150533 A1 Jun. 4, 2015

(30) Foreign Application Priority Data

Nov. 29, 2013 (JP) ................................. 2013-247933

(51) Int. Cl.
| | |
|---|---|
| *A61B 8/00* | (2006.01) |
| *B06B 1/06* | (2006.01) |
| *G10K 11/00* | (2006.01) |
| *A61B 8/14* | (2006.01) |
| *A61B 8/08* | (2006.01) |
| *G01S 15/89* | (2006.01) |

(52) U.S. Cl.
CPC ............ *A61B 8/4494* (2013.01); *A61B 8/145* (2013.01); *A61B 8/4427* (2013.01); *A61B 8/5207* (2013.01); *B06B 1/0622* (2013.01); *G01S 15/8918* (2013.01); *G10K 11/004* (2013.01)

(58) Field of Classification Search
None
See application file for complete search history.

(56) References Cited

U.S. PATENT DOCUMENTS

| | | | | |
|---|---|---|---|---|
| 3,833,825 | A * | 9/1974 | Haan ...................... | G10K 11/32 310/320 |
| 3,939,467 | A * | 2/1976 | Cook .................... | B06B 1/0644 310/320 |
| 4,382,201 | A * | 5/1983 | Trzaskos .............. | G10K 11/165 264/102 |
| 4,549,533 | A * | 10/1985 | Cain .................... | G10K 11/343 310/320 |

(Continued)

FOREIGN PATENT DOCUMENTS

| | | |
|---|---|---|
| CN | 103286056 A | 9/2013 |
| EP | 2527828 A1 | 11/2012 |

(Continued)

OTHER PUBLICATIONS

The Extended European Search Report for the corresponding European Application No. 14195110.3 dated Nov. 18, 2015.

*Primary Examiner* — Carolyn A Pehlke

(57) ABSTRACT

An ultrasonic device includes a substrate and a support member. The substrate has an element array including a plurality of ultrasonic transducer elements arranged in an array form. The support member has a surface adhered to the substrate in an area including the element array, and an opposite surface opposite from the surface adhered to the substrate, a distance from the surface adhered to the substrate to the opposite surface being different with respect to two adjacent ones of the ultrasonic transducer elements in the element array.

17 Claims, 13 Drawing Sheets

(56) References Cited

U.S. PATENT DOCUMENTS

| | | | | |
|---|---|---|---|---|
| 5,810,009 A | * | 9/1998 | Mine | B06B 1/0622 |
| | | | | 310/334 |
| 6,571,444 B2 | * | 6/2003 | Mauchamp | B06B 1/0622 |
| | | | | 29/25.35 |
| 8,973,443 B2 | | 3/2015 | Rhim et al. | |
| 2005/0075571 A1 | * | 4/2005 | Barnes | G10K 11/002 |
| | | | | 600/459 |
| 2011/0248603 A1 | | 10/2011 | Tezuka et al. | |
| 2012/0285250 A1 | | 11/2012 | Rhim et al. | |
| 2013/0223191 A1 | | 8/2013 | Nakamura et al. | |
| 2015/0099978 A1 | * | 4/2015 | Davidsen | A61B 8/4483 |
| | | | | 600/459 |
| 2015/0289843 A1 | * | 10/2015 | Wada | B06B 1/0622 |
| | | | | 600/459 |
| 2015/0298172 A1 | | 10/2015 | Nakamura et al. | |
| 2017/0136497 A1 | | 5/2017 | Nakamura et al. | |

FOREIGN PATENT DOCUMENTS

| | | | |
|---|---|---|---|
| JP | 10-227775 A | 8/1998 | |
| JP | 2010-042093 A | 2/2010 | |
| JP | WO 2014103593 A1 * | 7/2014 | B60B 1/0622 |
| JP | 2014-146883 A | 8/2014 | |
| WO | 2006/075283 A2 | 7/2006 | |

* cited by examiner

ULTRASONIC DEVICE, PROBE, ELECTRONIC EQUIPMENT, AND ULTRASONIC IMAGE DEVICE

CROSS-REFERENCE TO RELATED APPLICATIONS

This application claims priority to Japanese Patent Application No. 2013-247933 filed on Nov. 29, 2013. The entire disclosure of Japanese Patent Application No. 2013-247933 is hereby incorporated herein by reference.

BACKGROUND

Technical Field

The present invention relates to an ultrasonic device as well as a probe, electronic equipment, and ultrasonic image device or the like using that.

Related Art

As disclosed in Japanese Unexamined Patent Publication No. 2010-42093, an ultrasonic probe used for an ultrasonic image device such as an ultrasonic diagnostic device is generally known. Each ultrasonic transducer element is equipped with a so called bulk type piezoelectric layer, and an acoustic lens is fixed on the surface of the piezoelectric layer. When forming the ultrasonic image, ultrasonic signals are emitted from the acoustic lens.

The back surface of the piezoelectric layer is bonded to a backing layer. An ultrasonic absorption layer is formed within the backing layer. The ultrasonic absorption layer is sandwiched between an ultrasonic scattering member and an ultrasonic reflection layer. During emitting of ultrasonic vibrations, the ultrasonic vibrations of the piezoelectric layer are transmitted from the back surface to the ultrasonic absorption layer. Before advancing into the ultrasonic absorption layer, the ultrasonic vibrations pass through the ultrasonic scattering member. At the ultrasonic absorption layer, by the scattering and reflection of the ultrasonic waves being repeated, the ultrasonic waves are converted to thermal energy, and the thermal energy is transmitted to a heat transfer layer and a cooling layer. In this way, unnecessary ultrasonic vibrations are eliminated. When this kind of ultrasonic vibrations act on the piezoelectric layer, artifact is formed within the ultrasonic image.

SUMMARY

For preventing the appearance of a false image with the ultrasonic probe noted in Japanese Unexamined Patent Publication No. 2010-42093, on the back side of the piezoelectric layer, an ultrasonic transmission layer, an ultrasonic scattering member, an ultrasonic absorption layer, an ultrasonic reflection layer, a heat transfer layer and a cooling layer are formed. The structure of each ultrasonic transducer element and the ultrasonic probe become more complex. The structure becoming more complex leads to more complexity of the manufacturing steps.

Also, there was a desire for an ultrasonic device that can prevent the appearance of a false image within the ultrasonic image using a simple structure.

(1) An ultrasonic device according to one aspect includes a substrate and a support member. The substrate has an element array including a plurality of ultrasonic transducer elements arranged in an array form. The support member has a surface adhered to the substrate in an area including the element array, and an opposite surface opposite from the surface adhered to the substrate, a distance from the surface adhered to the substrate to the opposite surface being different with respect to two adjacent ones of the ultrasonic transducer elements in the element array.

Ultrasonic vibrations are emitted from the ultrasonic transducer element. The ultrasonic waves are emitted from a first surface of a substrate toward a subject such as a living body. At the same time, ultrasonic vibrations are transmitted from a second surface on the back side of the first surface to a support member. At the surface on the opposite side (hereafter called the "opposite surface") to the surface adhered to the substrate (hereafter called the "adhesive surface"), the ultrasonic waves are reflected according to the acoustic impedance of the medium in contact with the interface. At this time, with two adjacent ultrasonic transducer elements, the length of the ultrasonic wave transmission path to the opposite surface differs, so the ultrasonic waves that find their way to the ultrasonic transducer element are dispersed along the time axis. As a result, detection signals based on unnecessary ultrasonic vibrations are weakened with each ultrasonic transducer element. In this way it is possible to effectively prevent the appearance of a false image within the ultrasonic image according to the surface shape of the support member. In this way, the prevention of the appearance of a false image is realized with a simple structure. Also, "a distance . . . is different with respect to two adjacent ones of the ultrasonic transducer elements" means the thickness of the support member is different at the center of gravity positions of the respective ultrasonic transducer elements in a plan view along the thickness direction of the substrate.

(2) With the ultrasonic device, each of the ultrasonic transducer elements preferably includes a vibration plate supported on the substrate. The vibration plate is in contact with a space, and the space is positioned between the vibration plate and the support member, so the space is able to suppress the transmission of the ultrasonic vibrations from the vibration plate toward the support member. In this way, it is possible to have the ultrasonic vibrations transmitted from the vibration plate to the support member weakened.

(3) With the ultrasonic device, the opposite surface of the support member preferably defines an inclined plane that forms an angle with respect to the surface adhered to the substrate. If the inclined plane extends across two adjacent ultrasonic transducer elements, it is possible to easily differentiate the distance from the adhesive surface to the opposite surface with the formation of one inclined plane. In fact, the ultrasonic waves reflected from the opposite surface do not return on a vertical transmission path to the adhesive surface, but rather follow a transmission path inclined toward the adhesive surface. Consequently, the action of the ultrasonic waves on the ultrasonic transducer element is weakened according to the incline of the transmission path. In this way, it is possible to more effectively prevent the appearance of a false image within the ultrasonic image.

(4) With the ultrasonic device, the inclined plane preferably covers opening areas of the two adjacent ones of the ultrasonic transducer elements in a plan view along a thickness direction of the substrate. Detection signals based on unnecessary ultrasonic vibrations with each ultrasonic transducer element are reliably weakened. In this way, it is possible to effectively prevent the appearance of a false image within an ultrasonic image according to the surface shape of the support member. In this way, prevention of the appearance of false images is realized with a simple structure.

(5) With the ultrasonic device, the inclined plane is preferably inclined in a slice direction of the element array. With this kind of inclined plane, when one row of ultrasonic transducer elements emit ultrasonic waves simultaneously in the slice direction with an element array, it is possible to effectively prevent the appearance of a false image within an ultrasonic image.

(6) With the ultrasonic device, the inclined plane preferably covers the opening areas of the ultrasonic transducer elements included in a single row along the slice direction in the plan view. With this kind of inclined plane, when one row of ultrasonic transducer elements emit ultrasonic waves simultaneously in the slice direction with an element array, it is possible to effectively prevent the appearance of a false image within an ultrasonic image.

(7) With the ultrasonic device, the inclined plane is preferably inclined in a scan direction of the element array. With this kind of inclined plane, when one row of ultrasonic transducer elements emit ultrasonic waves simultaneously in the scan direction with an element array, it is possible to effectively prevent the appearance of a false image within an ultrasonic image.

(8) With the ultrasonic device, the inclined plane preferably covers the opening areas of the ultrasonic transducer elements arranged along the scan direction in the plan view and configured and arranged to be simultaneously driven. With this kind of inclined plane, when one row of ultrasonic transducer elements emit ultrasonic waves simultaneously in the scan direction with an element array, it is possible to effectively prevent the appearance of a false image within an ultrasonic image.

(9) With the ultrasonic device, the inclined plane is preferably a single inclined plane in the element array area in the plan view. With this kind of inclined plane, it is possible to form an incline in the slice direction as well as in the scan direction with one inclined plane.

(10) With the ultrasonic device, the support member preferably has a case coupling part with a height from the surface adhered to the substrate greater than a maximum distance from the surface adhered to the substrate to the inclined plane. The ultrasonic waves are attenuated by the case coupling part.

(11) With the ultrasonic device, the support member is preferably larger than the substrate in the plan view, the support member preferably has a bending rigidity larger than a bending rigidity of the substrate, and the surface adhered to the substrate is preferably flat. The support member reinforces the substrate, and it is possible to prevent deformation of the substrate by the working of the support member.

(12) With the ultrasonic device, each of the ultrasonic transducer elements preferably includes a piezoelectric element disposed on the vibration plate. When voltage is applied to the piezoelectric element, the piezoelectric element causes ultrasonic vibration of the vibration plate. The ultrasonic vibration of the vibration plate can be converted to electrical signals by the working of the piezoelectric element.

(13) The ultrasonic device can be used incorporated in a probe. At this time, the probe can be equipped with an ultrasonic device, and a case that supports the ultrasonic device.

(14) The ultrasonic device can be used incorporated in electronic equipment. At this time, the electronic equipment can be equipped with an ultrasonic device, and a processing unit that is connected to the ultrasonic device and configured to process the output of the ultrasonic device.

(15) The ultrasonic device can be used incorporated in an ultrasonic image device. At this time, the ultrasonic image device can be equipped with an ultrasonic device, a processing unit that is connected to the ultrasonic device and configured to process the output of the ultrasonic device and to generate an image, and a display device for displaying the image.

BRIEF DESCRIPTION OF THE DRAWINGS

Referring now to the attached drawings which form a part of this original disclosure.

DETAILED DESCRIPTION OF EXEMPLARY EMBODIMENTS

Hereafter, we will describe an embodiment of the present invention while referring to the attached drawings. This embodiment described hereafter does not unduly limit the contents of the present invention noted in the scope of patent claims, and all of the structures described with this embodiment are not absolutely necessary as means for solving of the present invention.

(1) Overall Configuration of the Ultrasonic Diagnostic Device

Figure 1:
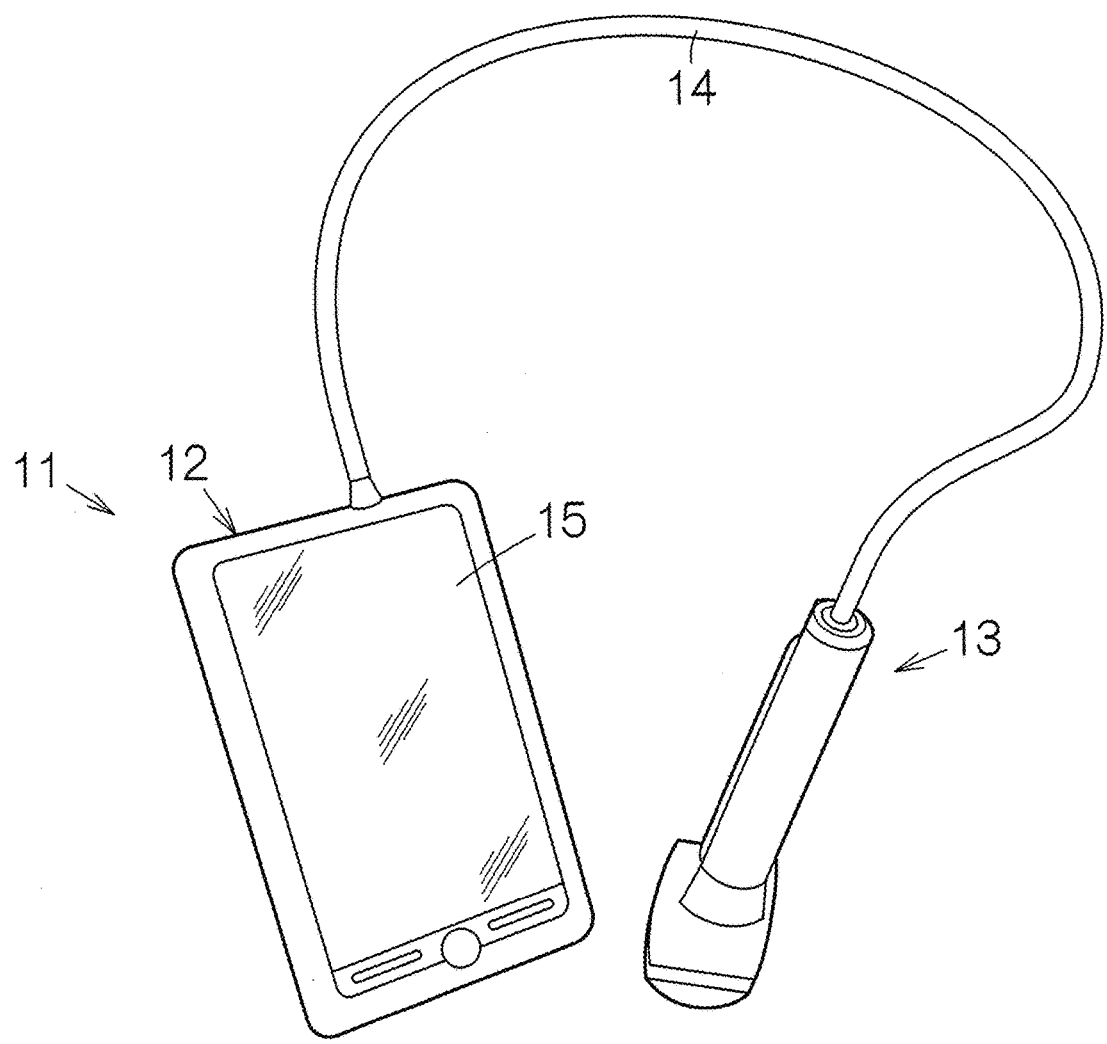
FIG. 1 is an external view schematically showing one example of the electronic equipment of an embodiment, specifically, an ultrasonic diagnostic device.

FIG. 1 schematically shows one example of electronic equipment of an embodiment of the present invention, specifically, the configuration of an ultrasonic diagnostic device (ultrasonic image device) 11. The ultrasonic diagnostic device 11 is equipped with a device terminal (processing unit) 12 and an ultrasonic probe (probe) 13. The device terminal 12 and the ultrasonic probe 13 are connected to each other by a cable 14. The device terminal 12 and the ultrasonic probe 13 exchange electronic signals through the cable 14. A display panel (display device) 15 is incorporated in the device terminal 12. The screen of the display panel 15 is exposed on the surface of the device terminal 12. With the device terminal 12, an image is generated based on the ultrasonic waves detected by the ultrasonic probe 13. The detected results put into image form are displayed on the screen of the display panel 15.

Figure 2:
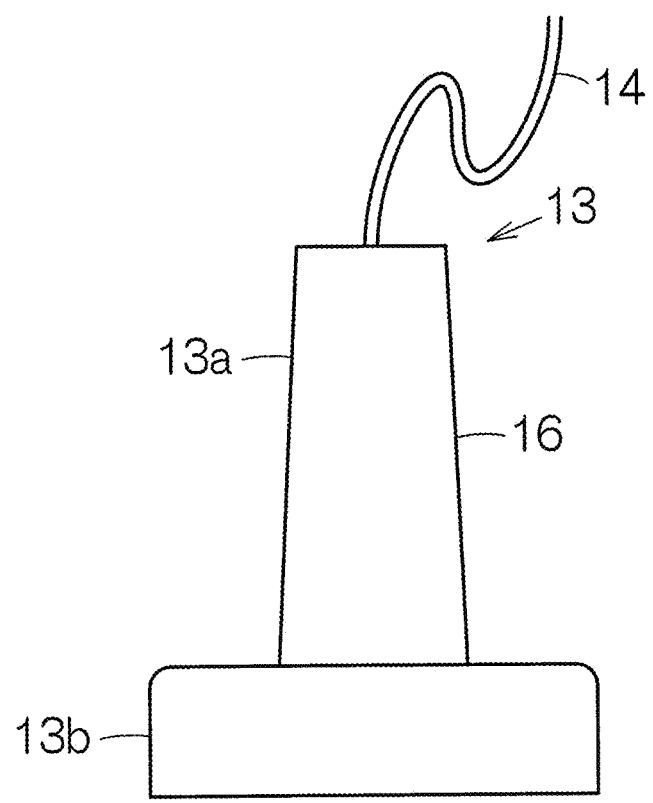
FIG. 2 is an enlarged front view of the ultrasonic probe.

As shown in FIG. 2, the ultrasonic probe 13 has a case 16. The case 16 divides a probe main unit 13a and a probe head 13b. This kind of probe main unit 13a and probe head 13a can be an integrated unit, or the probe head 13b can be linked so as to be freely detachable with the probe main unit 13a.

Figure 3:
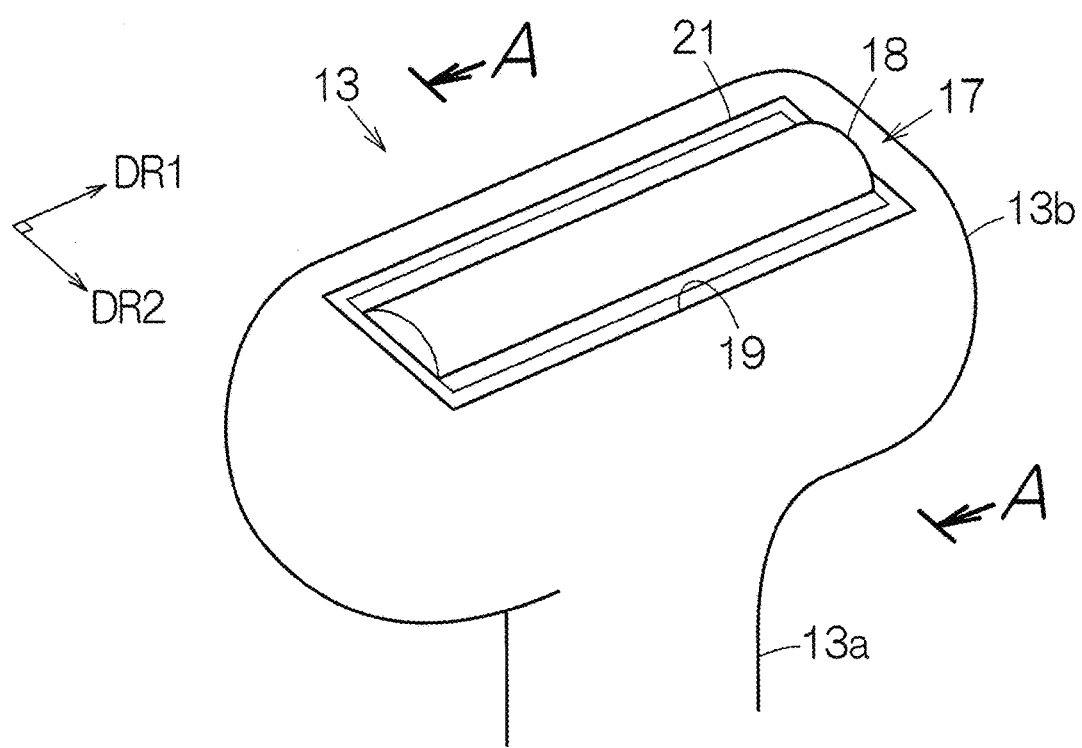
FIG. 3 is an enlarged perspective view of the probe head.

As shown in FIG. 3, an ultrasonic device 17 is incorporated in the probe head 13b. The ultrasonic device 17 is equipped with an acoustic lens 18. The acoustic lens 18 is exposed at the surface of the case 16. A partial cylindrical surface is formed on the outer surface of the acoustic lens 18. The curvature of the partial cylindrical surface is determined according to the focus position of the ultrasonic waves. The acoustic lens 18 is formed from silicone resin, for example. The acoustic lens 18 has acoustic impedance close to the acoustic impedance of the living body. The ultrasonic device 17 outputs ultrasonic waves from the surface of the acoustic lens 18 and also receives reflected waves of the ultrasonic waves.

An opening 19 is formed on the case 16. The acoustic lens 18 is arranged inside the opening 19. With the opening 19, a sealing material 21 is packed between the edge of the case 16 and the outer edge of the acoustic lens 18. In this way, sealing is realized along the outer edge of the acoustic lens 18. Here, a first direction DR1 is defined in parallel to the generatrix of the acoustic lens 18, and a second direction DR2 is defined that is orthogonal to the generatrix of the acoustic lens 18, and is in parallel to a virtual plane including the opening 19. The first direction DR1 and the second direction DR2 are mutually orthogonal within the virtual plane including the opening 19.

Figure 4:
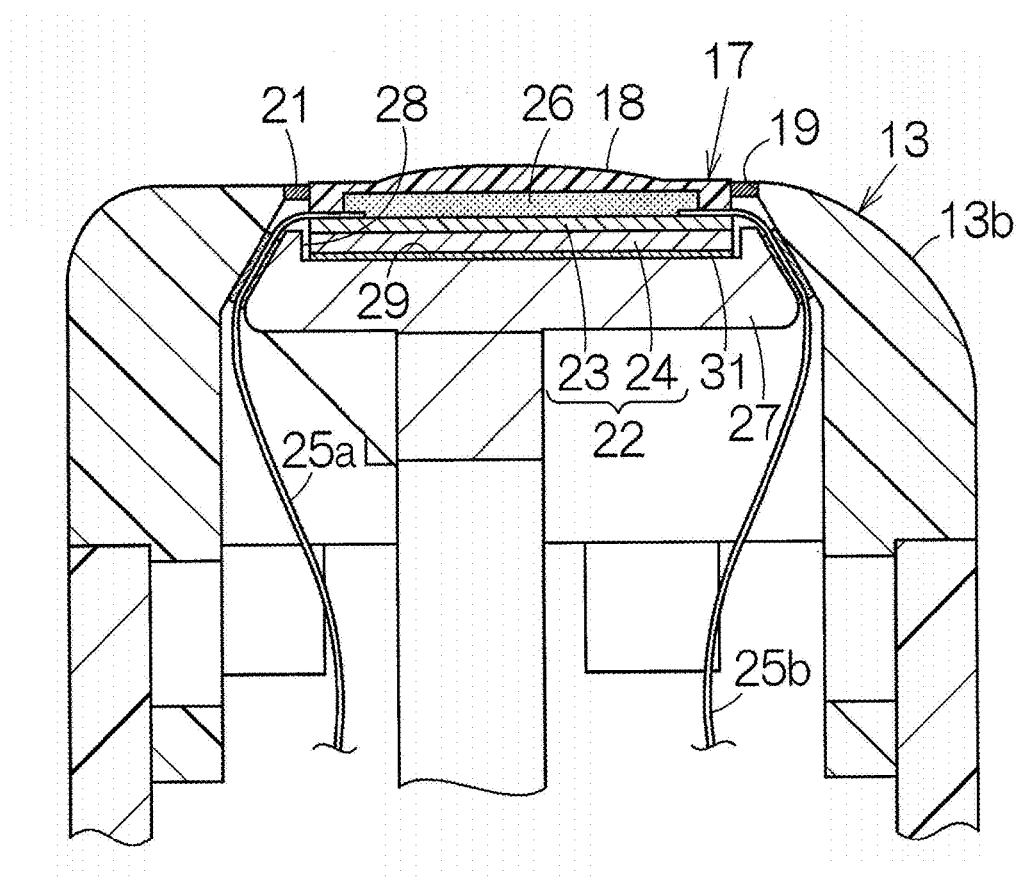
FIG. 4 is a vertical cross section view along line A-A of FIG. 3.

As shown in FIG. 4, the ultrasonic device 17 is equipped with a substrate 22. The substrate 22 has a substrate main unit 23. As is described later, ultrasonic transducer elements (hereafter called "elements") are formed on the substrate main unit 23. A backing material 24 is fixed to the back surface of the substrate main unit 23. The back surface of the substrate main unit 23 is overlapped on the surface of the backing material 24. The back surface of the substrate main unit 23 can be adhered to the back surface of the backing material 24. A first flexible printed circuits (hereafter called "first wiring board") 25a and a second flexible printed circuits (hereafter called "second wiring board") 25b are coupled to the substrate main unit 23. The first wiring board 25a and the second wiring board 25b are overlapped and coupled at the end part on the surface of the substrate main unit 23.

On the surface of the substrate 22, specifically, the surface of the substrate main unit 23, an acoustic matching layer 26 is laminated. The acoustic matching layer 26 covers the surface of the substrate main unit 23. A silicone resin film can be used for the acoustic matching layer 26, for example. The acoustic lens 18 is arranged on the acoustic matching layer 26. The acoustic lens 18 is tightly adhered to the surface of the acoustic matching layer 26. The acoustic lens 18 is adhered to the substrate 22 by the working of the acoustic matching layer 26.

The ultrasonic device 17 is equipped with a support member 27. The support member 27 is larger than the substrate 22 in the plan view along the thickness direction of the substrate 22 (hereafter simply called "plan view"), and has a larger bending rigidity than the bending rigidity of the substrate 22. The support member 27 can be formed from acrylic resin, for example. A depression 28 is formed on the support member 27. In the depression 28, a plane 29 is formed that is larger than the substrate 22 in the plan view. The substrate 22 is overlapped on this plane 29. The plane 29 is adhered to the substrate 22. For adhering, an adhesive agent 31 is used, for example. The support member 27 is coupled to the inside of the case 16. When coupling, the first wiring board 25a and the second wiring board 25b are sandwiched between the support member 27 and the case 16.

Figure 5:
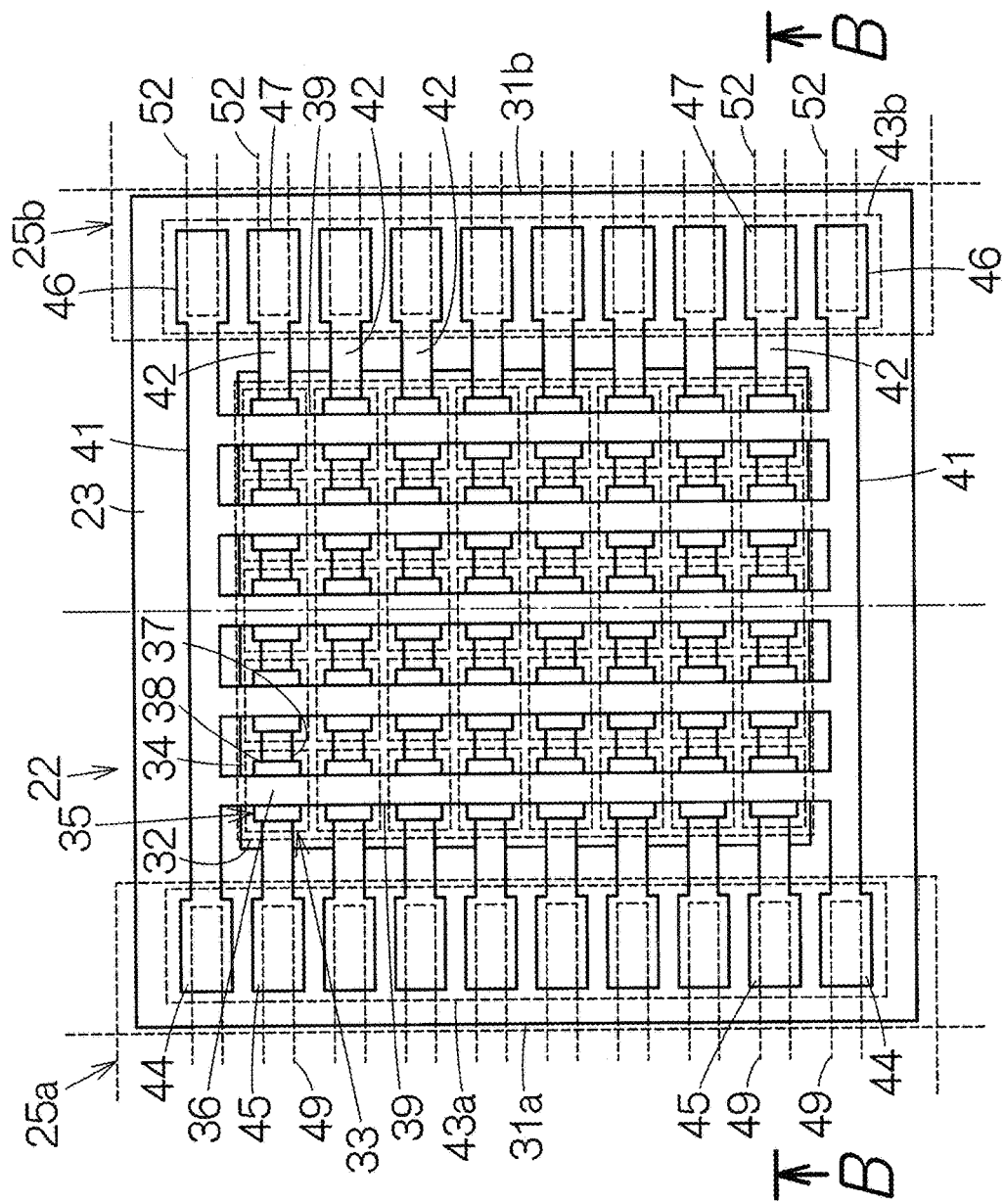
FIG. 5 is an enlarged plan view of the substrate.

FIG. 5 schematically shows a plan view of the substrate 22. The substrate 22 is equipped with a substrate main unit 23. An element array 32 is formed on the substrate main unit 23. The element array 32 is constituted with an array of elements 33 arranged in array form. The array is formed in a matrix of a plurality of rows and a plurality of columns. In addition, it is possible to establish a staggerd arrangement for the array. With a staggerd arrangement, the even numbered row element 33 group can be staggerd by a column pitch of ½ in relation to the odd numbered row element 33 group. The number of elements of one of the odd numbered row and the even numbered row can be one less than the number of elements of the other.

Each individual element 33 is equipped with a vibration plate 34. FIG. 5 depicts the outline of the vibration plate 34 with a dotted line in a plan view in the direction orthogonal to the film surface of the vibration plate 34 (plan view from the substrate thickness direction). A piezoelectric element 35 is formed on the top of the vibration plate 34. The piezoelectric element 35 is constituted with an upper electrode 36, a lower electrode 37, and a piezoelectric film 38. The piezoelectric film 38 is sandwiched between the upper electrode 36 and the lower electrode 37 for each element 33. These are overlapped in the sequence of the lower electrode 37, the piezoelectric film 38, and the upper electrode 36. The substrate 22 is constituted as one ultrasonic transducer element chip.

A plurality of first conductors 39 are formed on the surface of the substrate main unit 23. The first conductors 39 extend mutually in parallel to the column direction of the array. The column direction matches the second direction DR2, specifically, the slice direction. One first conductor 39 is allocated per column of elements 33. One first conductor 39 is connected in common to the piezoelectric film 38 of elements 33 aligned in the column direction of the array. The first conductor 39 has the upper electrode 36 formed for each individual element 33. Both ends of the first conductor 39 are respectively connected to a pair of lead-out wires 41. The lead-out wires 41 extend mutually in parallel in the row direction of the array. Therefore, all of the first conductors 39 have the same length. In this way, the upper electrodes 36 are connected in common to the elements 33 of the entire matrix. The first conductors 39 can be formed using iridium (Ir), for example. However, other conductive materials can also be used for the first conductors 39.

A plurality of second conductors 42 are formed on the surface of the substrate main unit 23. The second conductors 42 extend mutually in parallel to the row direction of the array. One second conductor 42 is allocated per row of elements 33. One second conductor 42 is arranged in common with the piezoelectric film 38 of the elements 33 aligned in the row direction of the array. The second conductor 42 has the lower electrode 37 formed for each individual element 33. For example, a laminated film of titanium (Ti), iridium (Ir), platinum (Pt), and titanium (Ti) can be used for the second conductor 42. However, it is also possible to use other conductive materials for the second conductor 42.

The energization of the elements 33 can be switched for each row. Linear scanning or sector scanning is realized according to this energization switching. Since one row of elements 33 output ultrasonic waves simultaneously, it is possible to determine the number of rows, specifically, the number of columns of the array, according to the ultrasonic wave output level. The number of columns can be set to approximately 10 to 30 columns, for example. This is abbreviated in the drawing with five columns depicted. The number of rows of the array can be determined according to the expansion of the scan range. The number of rows can be set to 128 rows or 256 rows, for example. This is abbreviated in the drawing with eight rows depicted. The role of the upper electrodes 36 and the lower electrodes 37 can also be interchanged. Specifically, while the lower electrodes are connected in common to the elements 33 of the entire matrix, the upper electrodes can be connected to the elements 33 in common for each row of the array. The curvature of the acoustic lens 18 is determined according to the focus position of the ultrasonic waves emitted from one row of elements 33 connected to one line of the second conductors 42.

The outline of the substrate main unit 23 has a first side 31a and a second side 31b facing opposite, partitioned by a pair of straight lines that are mutually parallel. One line of first terminal arrays 43a is arranged between the first side 31a and the element array 32 outline. One line of second terminal arrays 43b is arranged between the second side 31b and the element array 32 outline. The first terminal arrays 43a can be formed in one line in parallel to the first side 31a. The second terminal arrays 43b can be formed in one line in parallel to the second side 31b. The first terminal array 43a is constituted by one pair of upper electrode terminals 44 and a plurality of lower electrode terminals 45. Similarly, the second terminal array 43b is constituted by a pair of upper electrode terminals 46 and a plurality of lower electrode terminals 47. The upper electrode terminals 44 and 46 are respectively connected to both ends of one lead-out wire 41. The lead-out wire 41 and the upper electrode terminals 44 and 46 can be formed plane-symmetrically at the perpendicular plane that bisects the element array 32. The lower electrode terminals 45 and 47 are respectively connected to both ends of one second conductor 42. The second conductor 42 and the lower electrode terminals 45 and 47 can be formed plane-symmetrically at the perpendicular plane that bisects the element array 32. Here, the outline of the substrate main unit 23 is formed as a rectangle. The outline of the substrate main unit 23 can also be square or can be a trapezoid.

The first wiring board 25a is covered by the first terminal array 43a. A conductive line, specifically a first signal line 49, corresponding individually to the upper electrode terminal 44 and the lower electrode terminal 45, is formed on one end of the first wiring board 25a. The first signal line 49 is bonded separately facing to individually match the upper electrode terminal 44 and the lower electrode terminal 45. Similarly, a second flexible printed circuits 25b is covered on the base 21. The second wiring board 25b is covered by the second terminal array 43b. A conductive line, specifically, a second signal line 52, is formed corresponding individually to the upper electrode terminal 46 and the lower electrode terminal 47 at one end of the second wiring board 25b. The second signal line 52 is bonded separately facing to individually match the upper electrode terminal 46 and the lower electrode terminal 47.

Figure 6:
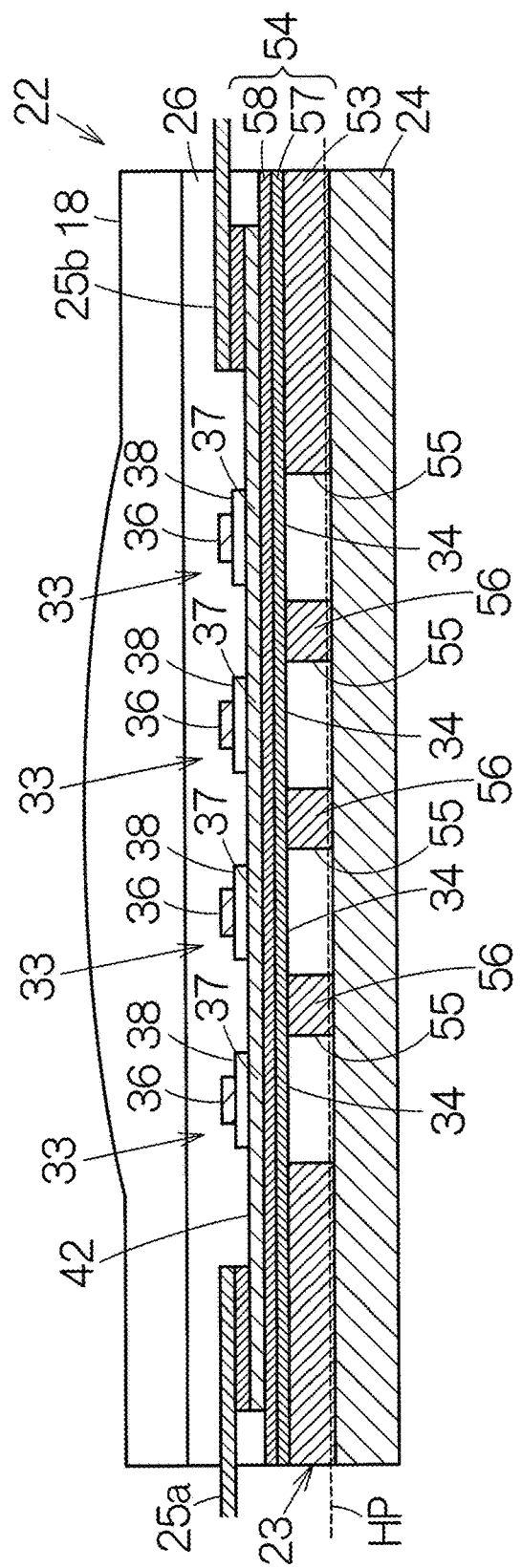
FIG. 6 is a cross section view along line B-B of FIG. 5.

As shown in FIG. 6, the substrate main unit 23 is equipped with a base material 53 and a coating film 54. The coating film 54 is formed over the entire surface on the surface of the base material 53. An opening 55 is formed for each individual element 33 on the base material 53. The openings 55 are arranged in array form on the base material 53. The outline of the area in which the openings 55 are arranged correlates to the outline of the element array 32. A partition wall 56 is demarcated between two adjacent openings 55. Adjacent openings 55 are partitioned by the partition wall 56. The wall thickness of the partition wall 56 correlates to the gap between the openings 55. The partition wall 56 defines two wall surfaces within the plane mutually extending in parallel. The wall thickness correlates to the distance between two wall surfaces. Specifically, the wall thickness can be regulated by the length of the perpendicular line sandwiched between the wall surfaces orthogonal to the wall surface. The base material 53 can be formed with a silicon substrate, for example. The backing material 24 closes the opening 55 on the back surface of the substrate main unit 23. The backing material 24 can be equipped with a rigid base material. Here, the partition wall 56 is coupled to the backing material 24. The backing material 24 is coupled at least at one coupling area location on each individual partition wall 56.

The coating film 54 is constituted by a silicon oxide ($SiO_2$) layer 57 laminated on the surface of the base material 53, and a zirconium oxide ($ZrO_2$) layer 58 laminated on the surface of the silicon oxide layer 57. The coating film 54 is in contact with the opening 55. In this way, a portion of the coating film 54 corresponding to the outline of the opening 55 forms the vibration plate 34. Of the coating film 54, the vibration plate 34 is the part for which it is possible to do film vibration in the thickness direction of the base material 53 since it faces the opening 55. The film thickness of the silicon oxide layer 57 can be determined based on the resonance frequency. The film thickness of the acoustic matching layer 26 is determined according to the resonance frequency of the vibration plate 34.

On the surface of the vibration plate 34 are laminated in sequence the lower electrode 37, the piezoelectric film 38, and the upper electrode 36. The piezoelectric film 38 can be formed using lead zircon titanate (PZT), for example. It is also possible to use another piezoelectric material for the piezoelectric film 38. Here, the piezoelectric film 38 completely covers the surface of the second conductor 42 below the first conductor 39. It is possible to avoid shorting between the first conductor 39 and the second conductor 42 by the working of the piezoelectric film 38.

(2) Support Member of the First Embodiment

Figure 7:
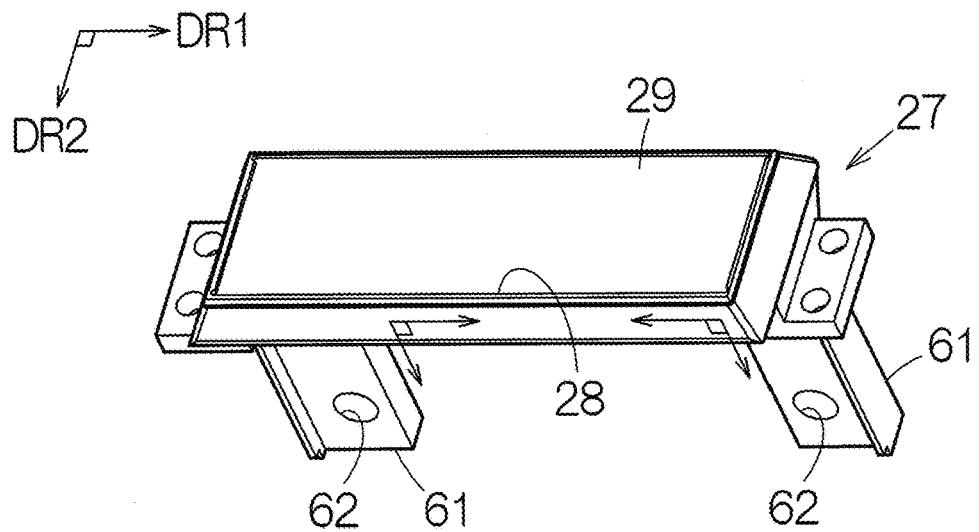
FIG. 7 is an enlarged perspective view of the support member of the first embodiment.

As shown in FIG. 7, with the support member 27, the outline of the plane 29 corresponds to the outline of the substrate 22 in a plan view. The plane 29 has a broadening that at least exceeds the outline of the substrate 22. Here, the outline of the plane 29 forms a rectangle. The plane 28 is formed as the bottom surface of the depression 28.

An attachment piece (case coupling part) 61 is formed as an integral unit on the support member 27. The attachment piece 61 extends in the direction orthogonal to the plane 29 so as to go away from the plane 29 from the back side of the plane 29 on the opposite side to the plane 29. A through hole 62 is formed on the attachment piece 61. The through hole 62 is formed in a cylinder shape having a center axis parallel to the second direction DR2 . An attachment screw (not illustrated) is inserted in the through hole 62. The support member 27 is fixed to the case 16 by the attachment screw.

Figure 8:
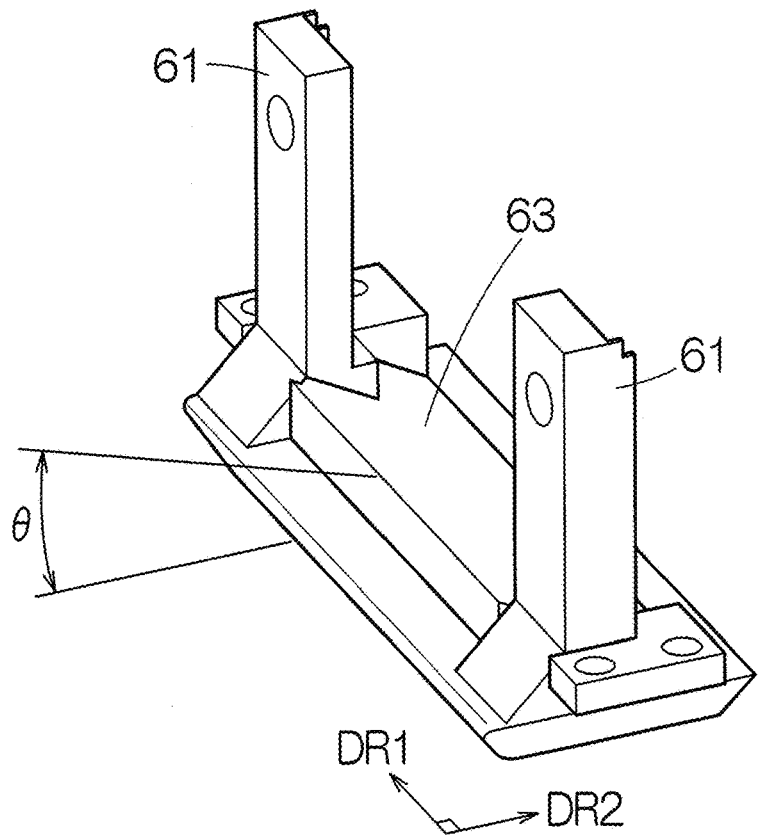
FIG. 8 is an enlarged perspective view of the support member observed from the back side of the plane.

As shown in FIG. 8, the support member 27 has a surface shape including an inclined plane 63. The inclined plane 63 forms an angle θ in relation to the plane 29 on the back side of the plane 29. The inclined plane 63 is inclined in the slice direction of the element array 32, specifically, the second direction DR2. Here, the inclined plane 63 is a single inclined plane in the area of the element array 32 in a plan view. Therefore, the inclined plane 63 is formed of a position and size including the opening area of one row of elements 33 in relation to the slice direction (second direction DR2) in a plan view. The attachment piece 61 has a greater height in terms of the height from the plane 29 than the height of the inclined plane 63. The height of the attachment piece 61 is preferably greater than the depth from the surface of the subject which is the image forming range.

Figure 9:
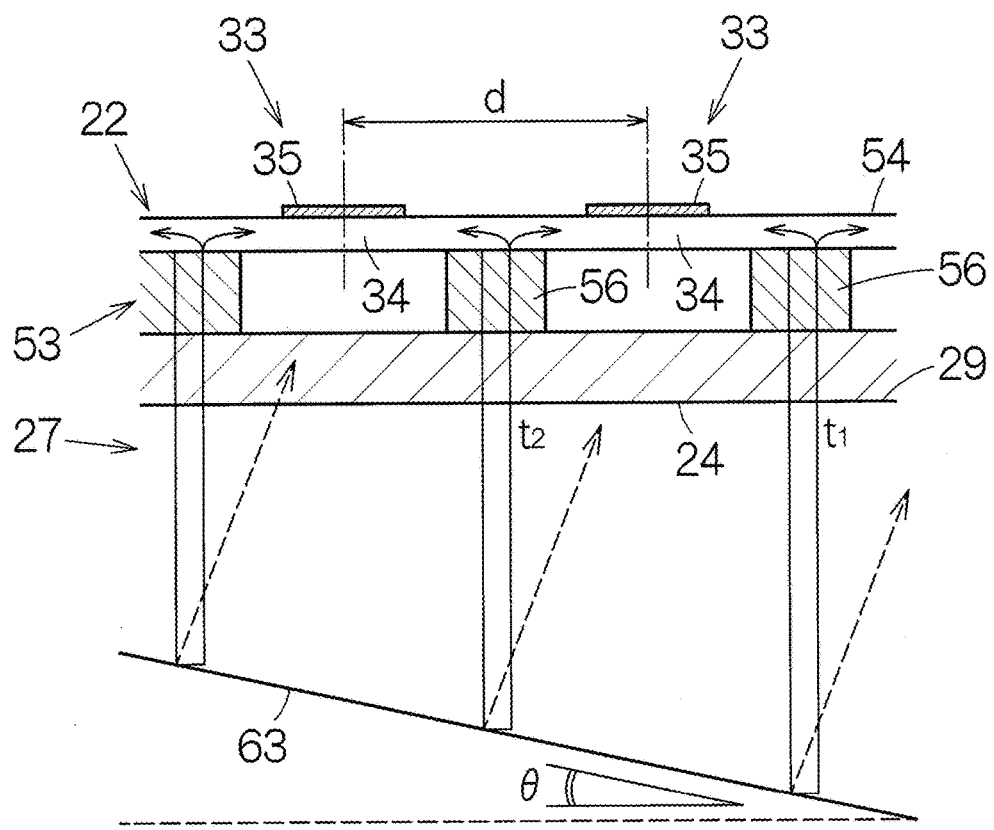
FIG. 9 is an enlarged view for schematically explaining the function of the inclined plane.

As shown in FIG. 9, with the support member 27, the distance from the plane 29 to the inclined plane 63 is different for two adjacent elements 33 in the slice direction (second direction DR2) in the element array 32. Specifically, in the plan view along the thickness direction of the substrate 22, the thickness of the support member 27 differs at the center of gravity position of the respective elements 33. At this time, according to the array pitch d (m) of the adjacent elements 33, the sound speed c (m/s) of the support member 27, and the angle θ (degree) of the inclined plane 63, the propagation time difference $t_1-t_2$ of the ultrasonic waves propagated from the element 33 to the support member 27, reflected by the inclined plane 63, and received at the element 33 is calculated using the following formulas.

Formula (1)

$$t_1 - t_2 = \frac{2d\tan\theta}{c} \quad (1)$$

The time when the time difference $t_1$-$t_2$ is a half cycle of the ultrasonic wave is when the cancellation effect is the greatest. Therefore, it is preferable to set an angle θ that satisfies Formula (3) based on Formula (2).

Formula (2)

$$\frac{1}{2f} = \frac{2d\tan\theta}{c} \quad (2)$$

Formula (3)

$$\theta = \tan^{-1}\frac{c}{4fd} \quad (3)$$

Here, f (Hz) is the frequency of the vibrating plate 34.

(3) Operation of the Ultrasonic Diagnostic Device

Next, we will give a brief description of the operation of the ultrasonic diagnostic device 11. For sending of ultrasonic waves, pulse signals are supplied to the piezoelectric element 35. The pulse signals are supplied to the elements 33 for each row through the lower electrode terminals 45 and 47 and the upper electrode terminals 44 and 46. With each element 33, an electric field acts on the piezoelectric film 38 between the lower electrode 37 and the upper electrode 36. The piezoelectric film 38 vibrates with the frequency of the ultrasonic waves. The vibration of the piezoelectric film 38 is conveyed to the vibration plate 34. In this way, when voltage is applied to the piezoelectric element 35, the vibration plate 34 does ultrasonic vibration. As a result, the desired ultrasonic beams are emitted toward the subject (e.g. the interior of a human body).

The reflected waves of the ultrasonic waves vibrate the vibration plate 34. The ultrasonic vibration of the vibration plate 34 causes ultrasonic vibration of the piezoelectric film 38 at a desired frequency. The ultrasonic vibrations of the vibration plate 34 are converted to electrical signals according to the piezoelectric effect of the piezoelectric element 35. Voltage is output from the piezoelectric element 35. Electric potential is generated between the upper electrode 36 and the lower electrode 37 with each element 33. The electric potential is output as electric signals from the lower electrode terminals 45 and 47 and the upper electrode terminals 44 and 46. In this way, ultrasonic waves are detected.

The sending and receiving of ultrasonic waves is repeated. As a result, linear scanning or sector scanning is realized. When scanning is completed, an image is formed based on the digital signals of the output signals. The formed image is displayed on the screen of the display panel 15.

Ultrasonic waves are emitted from the first surface of the substrate 22 toward the subject. At the same time, ultrasonic vibrations are transmitted from the second surface of the back side of the first surface to the support member 27. On the inclined plane 63 of the support member 27, air contacts the interface, so the propagated ultrasonic vibrations are reflected by the inclined plane 63. At this time, the length is different for the transmission paths of the ultrasonic vibrations to the inclined plane 63 with two adjacent elements 33, so the ultrasonic vibrations find their way to the elements 33 with a time difference. The ultrasonic vibrations that find their way to the elements 33 are dispersed along the time axis. As a result, the detection signals are weakened based on the unnecessary ultrasonic vibrations with each individual element 33. In this way, it is possible to effectively prevent the appearance of a false image within an ultrasonic image according to the surface shape of the support member 27. It is possible to realize prevention of the appearance of a false image using a simple structure.

With the ultrasonic device 17, the element 33 is equipped with a vibration plate 34. The vibration plate 34 contacts the space inside the opening 55. The space is positioned between the vibration plate 34 and the support member 27. The space can suppress the transmission of the ultrasonic vibrations from the vibration plate 34 toward the support member 27. In this way, it is possible to weaken the ultrasonic vibrations transmitted from the vibration plate 34 to the support member 27.

The inclined plane 63 extends across two adjacent elements 33. With the formation of one inclined plane 63, it is possible to easily differentiate the distance from the plane 29 to the surface of the opposite side. In fact, the ultrasonic waves reflected from the inclined plane 63 do not return on a vertical transmission path to the plane 29, but rather follow a transmission path inclined in relation to the plane 29. The action of the ultrasonic vibrations on the element 33 is weakened according to the incline of the transmission path. In this way, it is possible to more effectively prevent the appearance of a false image within the ultrasonic image.

The inclined plane 63 is formed at a position and size so as to include an opening area of two adjacent elements 33 in a plan view. Detection signals based on unnecessary ultrasonic vibrations with each element 33 are reliably weakened. In this way, it is possible to effectively prevent the appearance of a false image within an ultrasonic image according to the surface shape of the support member 27. In this way, prevention of the appearance of false images is realized with a simple structure.

With the ultrasonic device 17, the inclined plane 63 can be inclined in the slice direction, specifically, the second direction DR2. As described previously, with the element array 32, since one row of elements 33 emit ultrasonic waves simultaneously in the slice direction, the ultrasonic vibrations transmitted from one row of elements 33 are reflected by the inclined plane 63 and find their way to the elements 33 with a time difference. With this kind of inclined plane 63, it is possible to effectively prevent the appearance of a false image within an ultrasonic image.

As described previously, the inclined plane 63 can also be a single inclined plane that covers the entire area of the element array 32. The inclined plane 63 can be inclined not only in the slice direction as described previously, but can also be inclined in the scan direction. With this kind of inclined plane 63, it is possible to form an incline in the slice direction as well as the scan direction with one inclined plane.

With the support member 27, the attachment piece 61 has a greater height in terms of the height from the plane 29 than the height of the inclined plane 63. Therefore, even when ultrasonic vibrations are reflected by the tip of the attachment piece 61, the ultrasonic vibrations find their way through a long propagation path, so the ultrasonic vibrations are attenuated. For example, even when the attachment piece 61 is arranged within the area of the element array 32 in a plan view, it is possible to effectively prevent the appearance of a false image within the ultrasonic image.

The support member 27 is larger than the substrate 22 in the plan view. In addition, the support member 27 has a larger bending rigidity than the bending rigidity of the substrate 22. The support member 27 reinforces the substrate 22. The deformation of the substrate 22 can be prevented by the working of the support member 27.

(4) Testing

Figure 10:
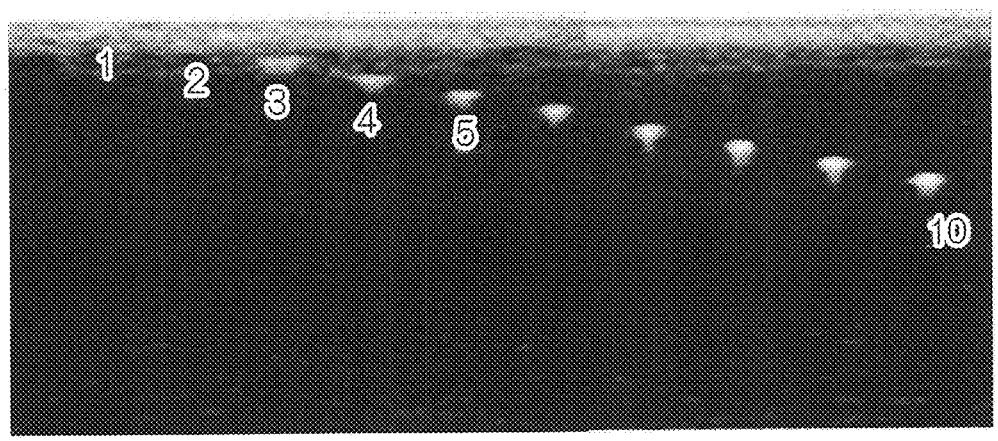
FIG. 10 is an example of an image showing the effect of the support member of the first embodiment.
Figure 11:
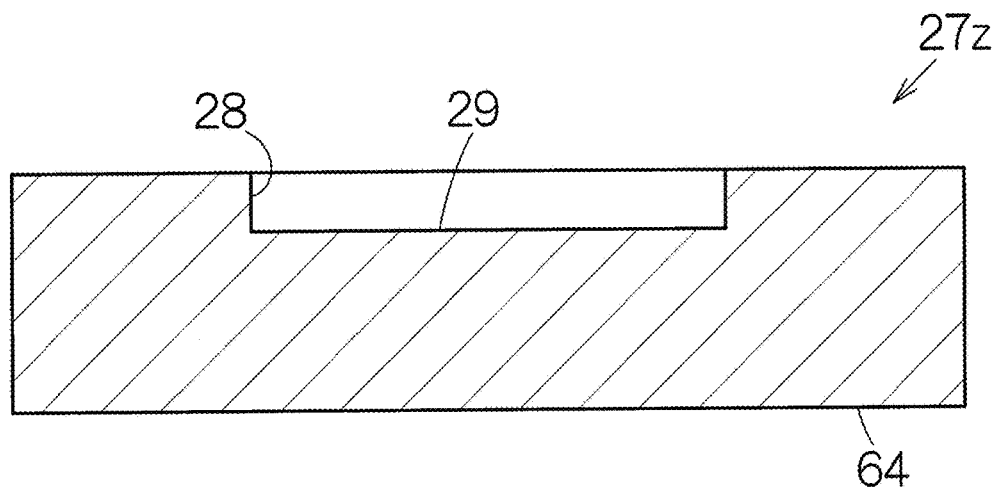
FIG. 11 is a schematic cross section of the support member of a comparative example.
Figure 12:
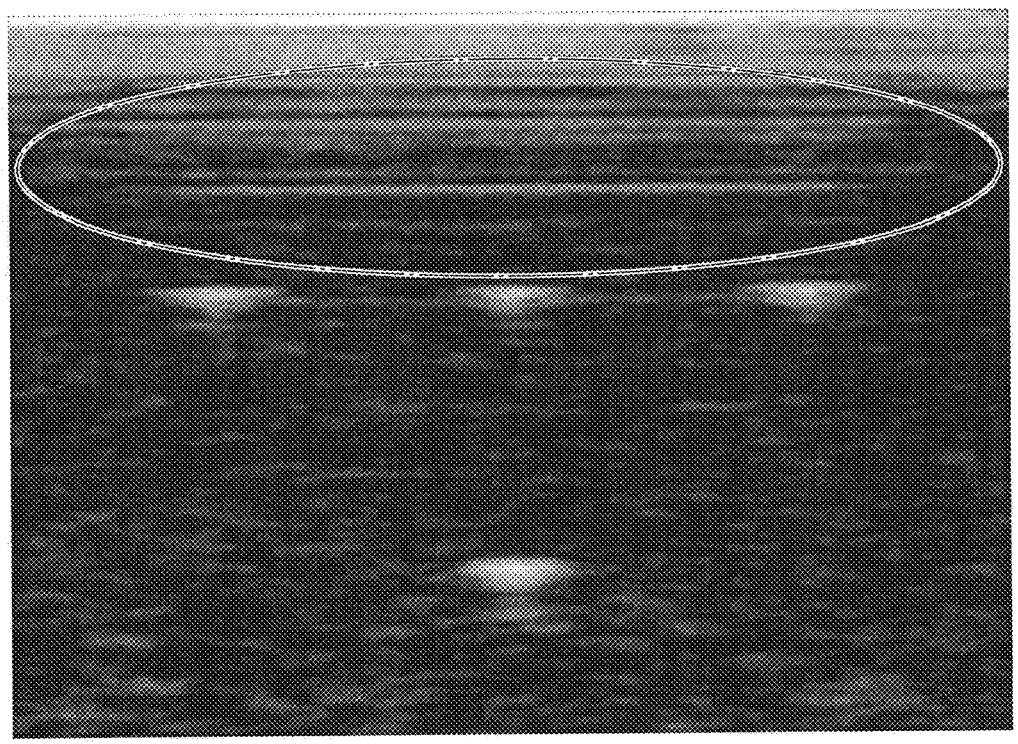
FIG. 12 is an example of an image showing the influence of the support member of the comparative example.

The inventors tested the effect of the support member 27. For testing, a virtual test subject was prepared. With the virtual test subject, a plurality of virtual targets were embedded in a silicone resin body. The virtual target was arranged at a specified depth from the surface of the silicone resin body. A plurality of depths were set. An ultrasonic image was created on the virtual test subject using the ultrasonic diagnostic device 11. As shown in FIG. 10, with this embodiment, it was confirmed that linear noise parallel to the surface of the virtual test subject was eliminated in the image. As shown in FIG. 11, the inventors prepared a support member 27z for the comparative example. With this support member 27z, a surface 64 that broadens in parallel to the plane 29 was formed on the back side of the plane 29. With the ultrasonic diagnostic device 11 described previously, the support member 27z was incorporated instead of the support member 27. As shown in FIG. 12, with the comparative example, linear noise parallel to the surface of the virtual test subject was seen.

(5) Support Member of the Second Embodiment

Figure 13:
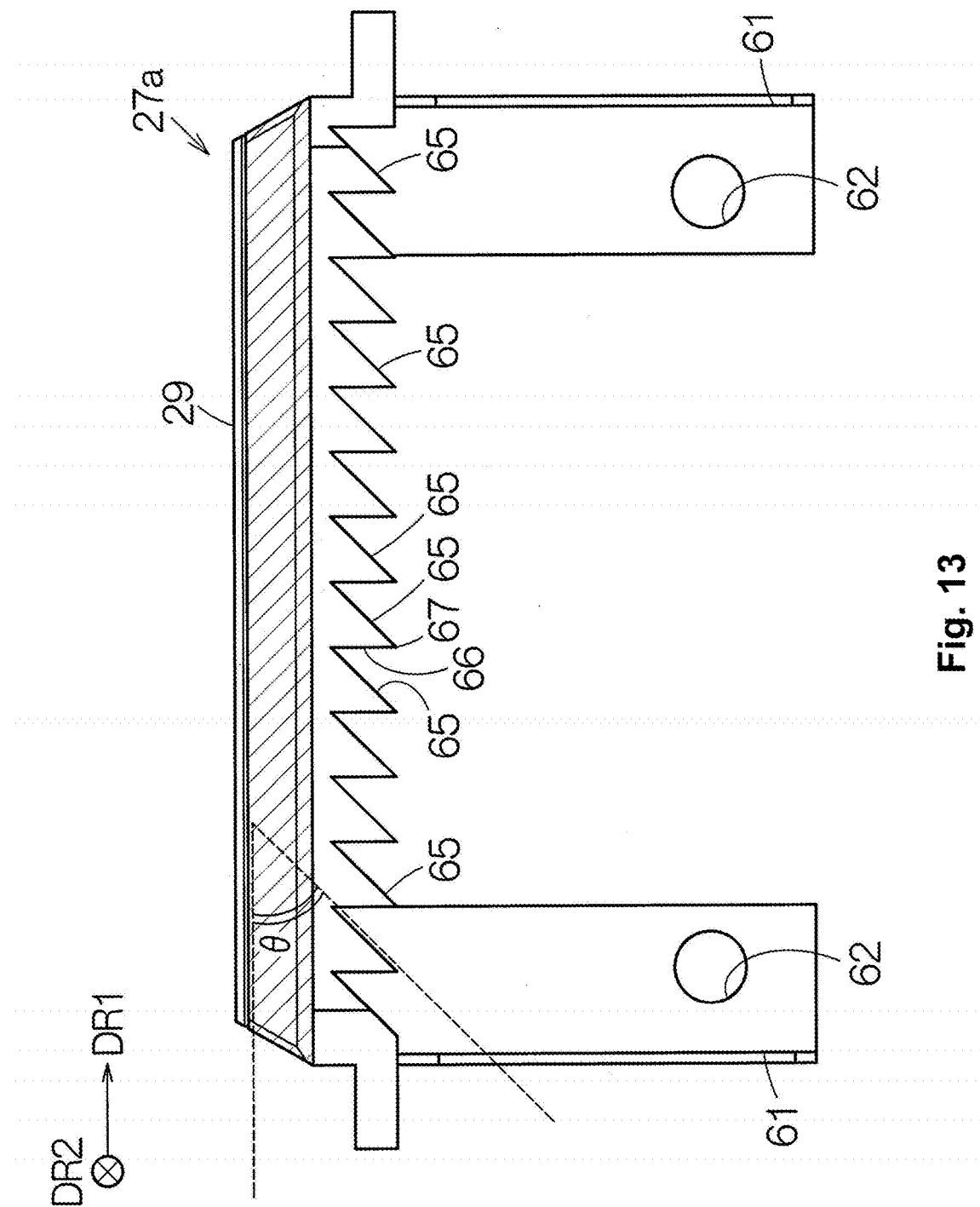
FIG. 13 is an enlarged cross section view of the support member of the second embodiment.

As shown in FIG. 13, a support member 27a of the second embodiment has a surface shape including an inclined plane 65. The inclined plane 65 forms an angle θ in relation to the plane 29 on the back side of the plane 29. The inclined plane 65 is inclined in the scan direction of the element array 32, specifically, the first direction DR1. The inclined plane 65 broadens in parallel to the slice direction, specifically, the second direction DR2. Here, the inclined plane 65 is divided into a plurality in the element array 32 area in the plan view based on the repeated shape of the scan direction (first direction DR 1). The thickness of the support member 27a is suppressed in the direction orthogonal to the plane 29 according to this kind of division. Two adjacent inclined planes 65 are connected to each other by a ridge line 67. With the support member 27a, for two adjacent elements 33 in the scan direction (first direction DR1) in the element array 32, the distance from the plane 29 to the inclined plane 65 in the element array 32 is different. The remainder of the constitution is the same as the support member 27 described previously.

When forming the ultrasonic image, about 15 rows to 30 rows of elements 33 simultaneously emit ultrasonic waves in the scan direction (first direction DR1). Ultrasonic waves are sent simultaneously from a plurality of elements 33 in the scan direction. The ultrasonic vibrations transmitted from a plurality of elements 33 are reflected by the inclined plane 65 and find their way to the elements 33 with a time difference. In this way, the inclined plane 65 is able to effectively prevent the appearance of a false image within the ultrasonic image. The inclined plane 65 is acceptable as long as it has a size that covers the opening area of the simultaneously driven elements 33.

Figure 14:
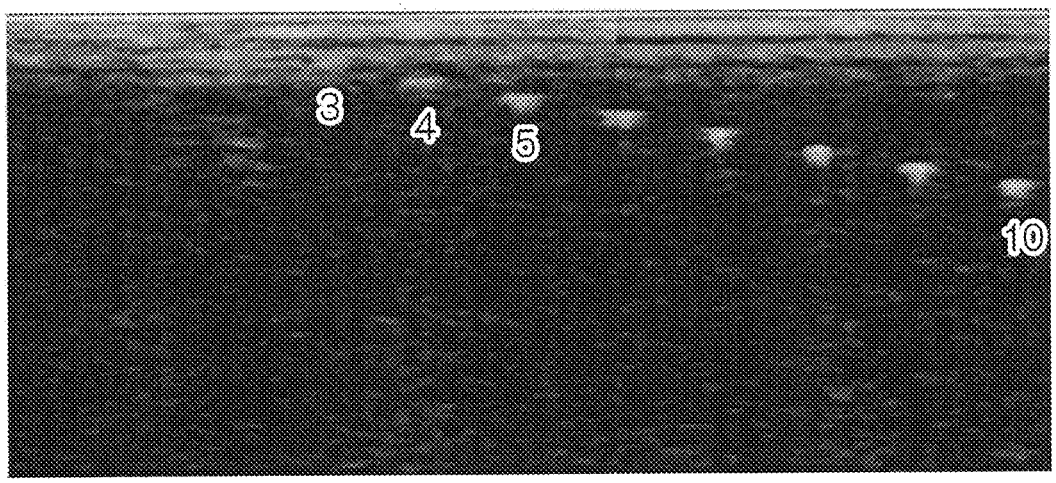
FIG. 14 is an example of an image showing the effect of the support member of the second embodiment.

The same as described previously, the inventors tested the effects of the support member 27a. For testing, the virtual test subject described previously was prepared. With the ultrasonic diagnostic device 11, the support member 27a was incorporated instead of the support member 27. As shown in FIG. 14, though an image remains based on the ultrasonic waves reflected by the ridge line 67 of the inclined plane 65 and the vertical surface 66, it was confirmed that the linear noise parallel to the surface of the virtual test subject in the image was mostly eliminated. However, compared to the support member 27 of the first embodiment, it was not possible to confirm a first depth and second depth virtual target.

(6) Support Member of the Third Embodiment

Figure 15:
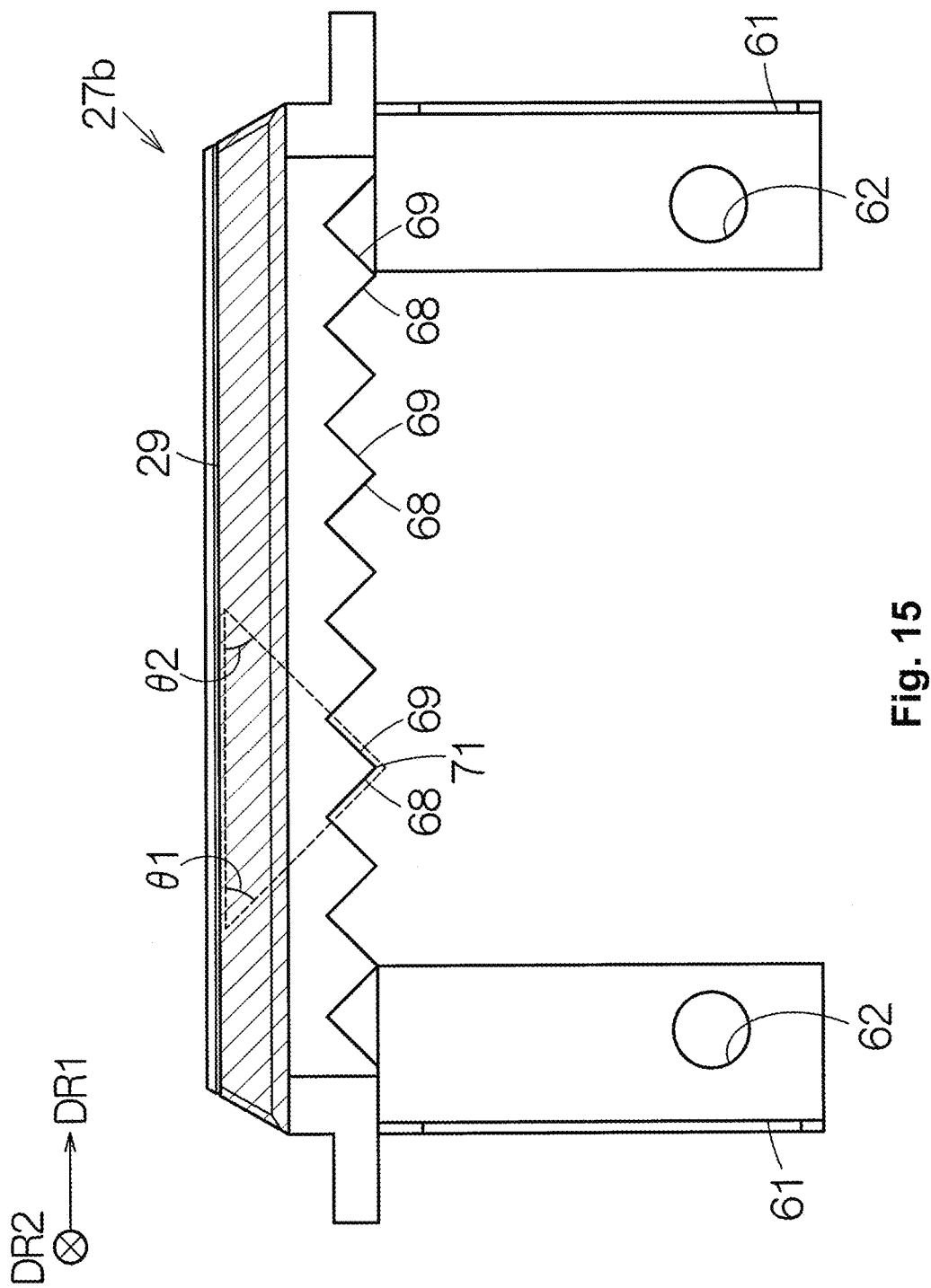
FIG. 15 is an enlarged cross section of the support member of the third embodiment.

As shown in FIG. 15, a support member 27b of the third embodiment has a surface shape including a first inclined plane 68 and a second inclined plane 69. The first inclined plane 68 forms an angle θ1 in relation to the plane 29 on the back side of the plane 29. The second inclined plane 69 forms an angle θ2 in relation to the plane 29 on the back side of the plane 29 facing opposite the first inclined plane 68. The angle θ1 and the angle θ2 can be equal. The first inclined plane 68 and the second inclined plane 69 are inclined in the scan direction of the element array 32, specifically, the first direction DR1. The first inclined plane 68 and the second inclined plane 69 broaden in parallel to the slice direction, specifically, the second direction DR2. Here, the first inclined plane 68 and the second inclined plane 69 are arranged continuously alternately in the scan direction (first direction DR1). The thickness of the support member 27b is suppressed in the direction orthogonal to the plane 29 according to the first inclined plane 68 and the second inclined plane 69 mutually facing opposite. The adjacent first inclined plane 68 and the second inclined plane 69 form a ridge line 71 and a valley line 72. With the support member 27b, for two adjacent elements 33 in the scan direction (first direction DR1) in the element array 32, the distance from the plane 29 to the inclined plane 68 and 69 differs within one inclined plane 68 and 69. The remainder of the constitution is the same as the previously described support member 27.

When forming the ultrasonic image, about 15 rows to 30 rows of elements 33 simultaneously emit ultrasonic waves in the scan direction (first direction DR1). Ultrasonic waves are sent simultaneously from a plurality of elements 33 in the scan direction. The ultrasonic vibrations transmitted from a plurality of elements 33 are reflected by the first inclined plane 68 and the second inclined plane 69 and find their way to the elements 33 with a time difference. In this way, the first inclined plane 68 and the second inclined plane 69 are able to effectively prevent the appearance of a false image within the ultrasonic image. The first inclined plane 68 and the second inclined plane 69 are acceptable as long as they respectively have a size that covers the opening area of the simultaneously driven elements 33.

Figure 16:
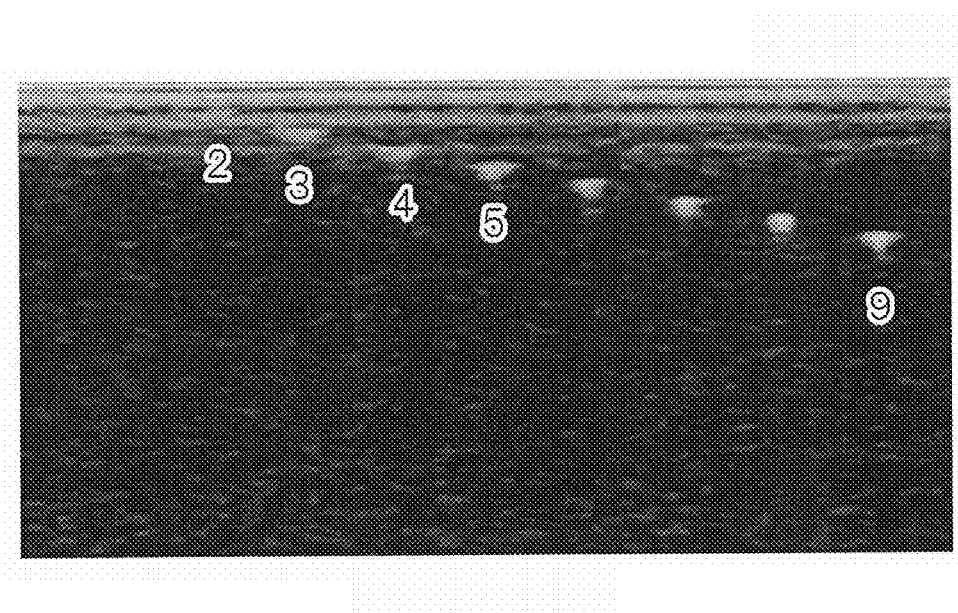
FIG. 16 is an example of an image showing the effect of the support member of the third embodiment.

The same as described previously, the inventors tested the effects of the support member 27b. For testing, the virtual test subject described previously was prepared. With the ultrasonic diagnostic device 11, the support member 27b was incorporated instead of the support member 27. As shown in FIG. 16, though an image remains based on the ultrasonic waves reflected by the ridge line 71 and the valley line 72 of the first inclined plane 68 and the second inclined plane 69, it was confirmed that the linear noise parallel to the surface of the virtual test subject in the image was mostly eliminated. However, compared to the support member 27 of the first embodiment, it was not possible to confirm a first depth virtual target.

We gave a detailed description of the embodiments as noted above, but a person skilled in the art will easily understand that it is possible to have many modifications without substantially straying from the novel items and effects of the present invention. Therefore, all of these kinds of modification examples are included within the scope of the present invention. For example, for terminology noted at least once together with a different term having a broader or the same meaning in the specification or drawings, that different terminology can be used as a substitute in any location in the specification or drawings. Also, the constitution and operation of the ultrasonic probe 13, the case 16, the ultrasonic device 17, the substrate 22, the elements 33 and the like are not limited to the items described with the embodiments, but can also have various modifications.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic device comprising:
    a substrate having an element array including a plurality of ultrasonic transducer elements arranged in an array form;
    an acoustic lens arranged on the substrate with a generatrix of the acoustic lens extending in a first direction; and
    a support member having a first surface facing and adhered to the substrate in an area including the element array, and a second surface facing an opposite direction from the first surface in a thickness direction of the substrate,
    the substrate defining a plurality of openings with each of the ultrasonic transducer elements being arranged in a corresponding one of the openings when viewed along the thickness direction of the substrate,
    each of the ultrasonic transducer elements including a vibration plate disposed between each of the ultrasonic transducer elements and each corresponding one of the openings, and
    a thickness of the support member between the first surface and the second surface being different at positions corresponding to centers of gravity of two adjacent ones of the ultrasonic transducer elements in the element array,
    the first surface of the support member being continuously flat, and
    the second surface of the support member defining a single, continuously inclined plane that forms an angle with respect to the first surface, the inclined plane being inclined in a second direction that is orthogonal to the generatrix of the acoustic lens, and the inclined plane corresponding to a plane connecting both ends of the second surface of the support member in the second direction.

2. The ultrasonic device according to claim 1, wherein the inclined plane overlaps the openings of the two adjacent ones of the ultrasonic transducer elements when viewed along the thickness direction of the substrate.

3. The ultrasonic device according to claim 2, wherein the inclined plane is parallel to the first direction.

4. The ultrasonic device according to claim 3, wherein the inclined plane overlaps the openings of the ultrasonic transducer elements included in a single row along the second direction when viewed along the thickness direction of the substrate.

5. The ultrasonic device according to claim 3, wherein the inclined plane is inclined in the first direction of the element array.

6. The ultrasonic device according to claim 5, wherein the inclined plane overlaps the openings of the ultrasonic transducer elements that are arranged along the first direction and are configured and arranged to be simultaneously driven when viewed along the thickness direction of the substrate.

7. The ultrasonic device according to claim 3, wherein a thickness of the support member between the first surface and the second surface being different at a position corresponding to a center of gravity in each of all ultrasonic transducer elements that are arranged along the second direction.

8. The ultrasonic device according to claim 2, wherein the second surface of the support member defines the single inclined plane covering an area of the element array when viewed along the thickness direction of the substrate.

9. The ultrasonic device according to claim 1, wherein the support member has a case coupling part, and a height of the case coupling part from the first surface is greater than a thickness of a thickest part of the support member in the thickness direction of the substrate.

10. The ultrasonic device according to claim 9, wherein a through hole is formed on the case coupling part.

11. The ultrasonic device according to claim 1, wherein an area of the support member is larger than an area of the substrate when viewed along the thickness direction of the substrate, and the support member has a bending rigidity larger than a bending rigidity of the substrate.

12. The ultrasonic device according to claim 1, wherein each of the ultrasonic transducer elements includes a piezoelectric element disposed on each of the vibration plates.

13. The ultrasonic device according to claim 1, wherein a depression is formed on the support member.

14. The ultrasonic device according to claim 1, wherein the inclined plane continuously covers an area of all the plurality of ultrasonic transducer elements included in the ultrasonic device when viewed along the thickness direction of the substrate.

15. A probe comprising:

the ultrasonic device according to claim 1, and a case supporting the ultrasonic device.

16. An electronic equipment comprising:

the ultrasonic device according to claim 1; and a processing unit connected to the ultrasonic device, and configured to process an output of the ultrasonic device.

17. An ultrasonic image device comprising:

the ultrasonic device according to claim 1;

a processing unit connected to the ultrasonic device, and configured to process an output of the ultrasonic device and to generate an image; and a display device configured and arranged to display the image.

* * * * *